(12) United States Patent
Chen et al.

(10) Patent No.: US 6,986,782 B2
(45) Date of Patent: Jan. 17, 2006

(54) AMBULATORY PHOTODYNAMIC THERAPY

(75) Inventors: James Chen, Bellevue, WA (US);
Brian Wilkerson, Issaquah, WA (US);
Dave Brown, Enumclaw, WA (US);
Darrin Huston, Enumclaw, WA (US);
Mike McQuade, Issaquam, WA (US)

(73) Assignee: Light Sciences Corporation, Snoqualmie, WA (US)

( * ) Notice: Subject to any disclaimer, the term of this patent is extended or adjusted under 35 U.S.C. 154(b) by 259 days.

(21) Appl. No.: 10/211,784

(22) Filed: Aug. 1, 2002

(65) Prior Publication Data

US 2002/0198576 A1 Dec. 26, 2002

Related U.S. Application Data

(62) Division of application No. 09/232,129, filed on Jan. 15, 1999, now Pat. No. 6,454,789.

(51) Int. Cl.
*A61N 5/06* (2006.01)

(52) U.S. Cl. .......................... 607/88; 607/92; 362/572; 362/574

(58) Field of Classification Search ............. 607/88–93; 606/2, 13–18; 362/572–574
See application file for complete search history.

(56) References Cited

U.S. PATENT DOCUMENTS

| | | | |
|---|---|---|---|
| 2,797,213 A | 6/1957 | Moore | 260/141 |
| 3,046,118 A | 7/1962 | Schmidt | 96/33 |
| 3,046,120 A | 7/1962 | Schmidt | 96/33 |
| 4,337,759 A | 7/1982 | Popovich et al. | 126/438 |
| 4,675,338 A | 6/1987 | Bommer et al. | 514/410 |

(Continued)

FOREIGN PATENT DOCUMENTS

| | | |
|---|---|---|
| AU | 0674251 | 12/1996 |
| AU | 0694868 | 7/1998 |
| AU | 0708410 | 8/1999 |
| AU | 0713227 | 11/1999 |
| AU | 0720815 | 6/2000 |
| AU | 0721857 | 7/2000 |
| EP | 0407122 | 1/1991 |

(Continued)

OTHER PUBLICATIONS

Beems et al., "Photosensitizing properties of bacteriochlorophyllin a and bacteriochlorin a, two derivatives of bacteriochlorophyll a", *Photochem. Photobiol.*, 46(5):639–643 (1987).

Bellnier et al., "Murine pharmacokinetics and antitumor efficacy of the photodynamic sensitizer 2-[1-hexyloxyethyl]-2-devinyl pyropheophorbide-a", *J. Photochem. Photobiol. B: Biol.*, 20:55–61 (1993).

(Continued)

*Primary Examiner*—Roy D. Gibson
(74) *Attorney, Agent, or Firm*—Ronald M. Anderson

(57) ABSTRACT

Methods for delivering light to a treatment site of a patient to administer a light therapy thereto are provided. A method includes steps of providing a portable power source, and a light source configured to provide light suitable for the light therapy for a period of at least two hours, and an optical fiber; positioning a distal portion of the optical fiber that is adapted to be disposed at the treatment site within a patient's body, where the light generated by the light source and conveyed by the optical fiber exits from the distal portion of the optical fiber; energizing the light source with the portable power supply; and administering the light treatment to the treatment site with the light source, wherein the patient is ambulatory without interruption of the light therapy during the treatment.

16 Claims, 7 Drawing Sheets

U.S. PATENT DOCUMENTS

| | | | |
|---|---|---|---|
| 4,693,556 A | 9/1987 | McCaughan, Jr. | 350/320 |
| 4,693,885 A | 9/1987 | Bommer et al. | 424/2 |
| 4,746,840 A * | 5/1988 | Lim | 315/58 |
| 4,753,958 A | 6/1988 | Weinstein et al. | 514/410 |
| 4,823,244 A | 4/1989 | Alaybayoglu et al. | 362/194 |
| 4,849,207 A | 7/1989 | Sakata et al. | 424/1.1 |
| 4,932,934 A | 6/1990 | Dougherty et al. | 604/21 |
| 4,998,930 A | 3/1991 | Lundahl | 606/15 |
| 5,002,962 A | 3/1991 | Pandey et al. | 514/410 |
| 5,026,367 A | 6/1991 | Leckrone et al. | 606/7 |
| 5,055,446 A | 10/1991 | Alexander et al. | 514/2 |
| 5,169,395 A * | 12/1992 | Narciso, Jr. | 606/7 |
| 5,171,749 A | 12/1992 | Levy et al. | 514/410 |
| 5,190,536 A | 3/1993 | Wood et al. | 606/16 |
| 5,209,748 A * | 5/1993 | Daikuzono | 606/16 |
| 5,263,925 A | 11/1993 | Gilmore et al. | 604/4 |
| 5,283,255 A | 2/1994 | Levy et al. | 514/410 |
| 5,314,905 A | 5/1994 | Pandey et al. | 514/410 |
| 5,320,618 A * | 6/1994 | Gustafsson | 606/9 |
| 5,344,434 A | 9/1994 | Talmore | 607/88 |
| 5,399,583 A | 3/1995 | Levy et al. | 514/410 |
| 5,404,869 A | 4/1995 | Parkyn, Jr. et al. | 126/699 |
| 5,445,608 A | 8/1995 | Chen et al. | 604/20 |
| 5,454,794 A * | 10/1995 | Narciso et al. | 607/88 |
| 5,456,661 A | 10/1995 | Narciso, Jr. | 604/20 |
| 5,474,528 A | 12/1995 | Meserol | 604/20 |
| 5,474,765 A | 12/1995 | Thorpe | 424/178.17 |
| 5,482,698 A | 1/1996 | Griffiths | 424/1.41 |
| 5,484,778 A | 1/1996 | Kenney et al. | 514/63 |
| 5,484,803 A | 1/1996 | Richter | 514/410 |
| 5,491,765 A * | 2/1996 | Matsumoto | 385/33 |
| 5,494,793 A | 2/1996 | Schindele et al. | 435/6 |
| 5,514,669 A | 5/1996 | Selman | 514/63 |
| 5,519,534 A | 5/1996 | Smith et al. | 359/599 |
| 5,543,514 A | 8/1996 | Sessler et al. | 540/472 |
| 5,565,552 A | 10/1996 | Magda et al. | 534/11 |
| 5,571,152 A | 11/1996 | Chen et al. | 607/92 |
| 5,576,013 A | 11/1996 | Williams et al. | 424/423 |
| 5,577,492 A | 11/1996 | Parkyn, Jr. et al. | 126/698 |
| 5,577,493 A | 11/1996 | Parkyn, Jr. et al. | 126/699 |
| 5,591,855 A | 1/1997 | Hudkins et al. | 546/256 |
| 5,594,136 A | 1/1997 | Sessler et al. | 540/472 |
| 5,613,769 A | 3/1997 | Parkyn, Jr. et al. | 362/338 |
| 5,616,140 A | 4/1997 | Prescott | 606/10 |
| 5,630,996 A | 5/1997 | Reno et al. | 424/1.49 |
| 5,634,711 A | 6/1997 | Kennedy et al. | 362/119 |
| 5,643,334 A | 7/1997 | Eckhouse et al. | 607/88 |
| 5,645,562 A | 7/1997 | Haan et al. | 606/194 |
| 5,655,832 A | 8/1997 | Pelka et al. | 362/296 |
| 5,676,453 A | 10/1997 | Parkyn, Jr. et al. | 362/260 |
| 5,686,113 A | 11/1997 | Speaker et al. | 424/490 |
| 5,698,866 A | 12/1997 | Doiron et al. | 257/99 |
| 5,700,243 A | 12/1997 | Nariso, Jr. | 604/102 |
| 5,702,432 A | 12/1997 | Chen et al. | 607/88 |
| 5,703,896 A | 12/1997 | Pankove et al. | 372/50 |
| 5,705,518 A | 1/1998 | Richter et al. | 514/410 |
| 5,707,401 A | 1/1998 | Talmore | 607/88 |
| 5,709,653 A | 1/1998 | Leone | 604/20 |
| 5,715,837 A | 2/1998 | Chen | 128/899 |
| 5,735,817 A | 4/1998 | Shantha | 604/100 |
| 5,736,563 A | 4/1998 | Richter | 514/410 |
| 5,741,316 A | 4/1998 | Chen et al. | 607/61 |
| 5,746,494 A | 5/1998 | Koeda et al. | 362/32 |
| 5,746,495 A | 5/1998 | Klamm | 362/32 |
| 5,757,557 A | 5/1998 | Medvedev et al. | 359/708 |
| 5,766,222 A | 6/1998 | Petit | 606/234 |
| 5,766,234 A | 6/1998 | Chen et al. | 607/92 |
| 5,769,844 A | 6/1998 | Ghaffari | 606/16 |
| 5,770,730 A | 6/1998 | Pandey et al. | 540/472 |
| 5,775,339 A | 7/1998 | Woodburn et al. | 128/898 |
| 5,776,175 A | 7/1998 | Eckhouse et al. | 607/100 |
| 5,776,427 A | 7/1998 | Thorpe et al. | 424/1.49 |
| 5,782,896 A | 7/1998 | Chen et al. | 607/88 |
| 5,797,868 A | 8/1998 | Leone | 604/21 |
| 5,798,349 A | 8/1998 | Levy et al. | 514/185 |
| 5,800,478 A | 9/1998 | Chen et al. | 607/88 |
| 5,803,575 A | 9/1998 | Ansems et al. | 362/32 |
| 5,806,955 A | 9/1998 | Parkyn, Jr. et al. | 362/31 |
| 5,807,881 A | 9/1998 | Leong et al. | 514/410 |
| 5,811,248 A | 9/1998 | Ditlow et al. | 435/7.9 |
| 5,814,008 A | 9/1998 | Chen et al. | 604/21 |
| 5,817,048 A | 10/1998 | Lawandy | 604/20 |
| 5,824,657 A | 10/1998 | Hill et al. | 514/46 |
| 5,827,186 A | 10/1998 | Chen et al. | 600/407 |
| 5,829,448 A | 11/1998 | Fisher et al. | 128/898 |
| 5,835,648 A | 11/1998 | Narciso, Jr. et al. | 385/31 |
| 5,843,143 A | 12/1998 | Whitehurst | 607/88 |
| 5,849,027 A | 12/1998 | Gart et al. | 607/93 |
| 5,851,225 A | 12/1998 | Lawandy | 607/88 |
| 5,855,866 A | 1/1999 | Thorpe et al. | 424/1.49 |
| 5,863,538 A | 1/1999 | Thorpe et al. | 424/136.1 |
| 5,864,035 A | 1/1999 | Pandey et al. | 540/472 |
| 5,865,840 A | 2/1999 | Chen | 607/92 |
| 5,876,427 A | 3/1999 | Chen et al. | 607/88 |
| 5,881,200 A | 3/1999 | Burt | 385/142 |
| 5,882,328 A | 3/1999 | Levy et al. | 604/20 |
| 5,882,779 A | 3/1999 | Lawandy | 428/323 |
| 5,906,579 A | 5/1999 | Vander Salm et al. | 600/424 |
| 5,909,670 A | 6/1999 | Trader et al. | 705/14 |
| 5,912,257 A | 6/1999 | Prasad et al. | 514/356 |
| 5,913,834 A | 6/1999 | Francais | 600/591 |
| 5,913,884 A | 6/1999 | Trauner et al. | 607/88 |
| 5,919,217 A | 7/1999 | Hughes | 607/90 |
| 5,921,244 A | 7/1999 | Chen et al. | 128/897 |
| 5,924,788 A | 7/1999 | Parkyn, Jr. | 362/329 |
| 5,926,320 A | 7/1999 | Parkyn, Jr. et al. | 359/641 |
| 5,929,105 A | 7/1999 | Sternberg et al. | 514/410 |
| 5,942,534 A | 8/1999 | Trauner et al. | 514/410 |
| 5,943,354 A | 8/1999 | Lawandy | 372/39 |
| 5,945,762 A | 8/1999 | Chen et al. | 310/171 |
| 5,952,329 A | 9/1999 | Cincotta et al. | 514/224.5 |
| 5,957,960 A | 9/1999 | Chen et al. | 607/92 |
| 5,961,543 A | 10/1999 | Waldmann | 607/88 |
| 5,976,175 A | 11/1999 | Hirano et al. | 607/89 |
| 5,985,353 A | 11/1999 | Lawton et al. | 427/2.13 |
| 5,989,245 A | 11/1999 | Prescott | 606/14 |
| 5,990,479 A | 11/1999 | Weiss et al. | 250/307 |
| 5,997,569 A | 12/1999 | Chen et al. | 607/88 |
| 5,997,842 A | 12/1999 | Chen | 424/1.29 |
| 6,013,053 A | 1/2000 | Bower et al. | 604/96 |
| 6,015,897 A | 1/2000 | Theodore et al. | 540/474 |
| 6,021,347 A | 2/2000 | Herbst et al. | 607/2 |
| 6,048,359 A * | 4/2000 | Biel | 607/92 |
| 6,051,230 A | 4/2000 | Thorpe et al. | 424/178.1 |
| 6,058,937 A | 5/2000 | Doiron et al. | 128/898 |
| 6,071,944 A | 6/2000 | Rodgers et al. | 514/408 |
| 6,080,160 A | 6/2000 | Chen et al. | 606/72 |
| 6,083,485 A | 7/2000 | Licha et al. | 424/9.6 |
| 6,092,531 A | 7/2000 | Chen et al. | 128/899 |
| 6,096,066 A | 8/2000 | Chen et al. | 607/88 |
| 6,100,290 A | 8/2000 | Levy et al. | 514/410 |
| 6,100,893 A | 8/2000 | Ensz et al. | 345/420 |
| 6,107,325 A | 8/2000 | Chan et al. | 514/410 |
| 6,135,620 A | 10/2000 | Marsh | 362/377 |
| 6,138,681 A | 10/2000 | Chen et al. | 128/899 |
| 6,165,440 A | 12/2000 | Esenaliev | 424/1.11 |
| 6,183,444 B1 | 2/2001 | Glines et al. | 604/187 |
| 6,210,425 B1 | 4/2001 | Chen | 607/88 |
| 6,217,869 B1 | 4/2001 | Meyer et al. | 424/178.1 |
| 6,238,426 B1 | 5/2001 | Chen | 607/88 |
| 6,273,904 B1 | 8/2001 | Chen et al. | 607/88 |

| | | | |
|---|---|---|---|
| 6,281,611 B1 | 8/2001 | Chen et al. ............... 310/171 |
| 6,297,228 B1 | 10/2001 | Clark ...................... 514/177 |
| 6,319,273 B1 | 11/2001 | Chen et al. ................ 607/88 |
| 6,331,744 B1 | 12/2001 | Chen et al. ............... 310/171 |
| 6,344,050 B1 | 2/2002 | Chen ......................... 607/88 |
| 6,416,531 B2 | 7/2002 | Chen ......................... 607/89 |
| 6,429,936 B1 * | 8/2002 | Scaduto ..................... 356/417 |
| 6,454,789 B1 | 9/2002 | Chen ......................... 607/88 |
| 6,520,669 B1 | 2/2003 | Chen et al. ................ 362/545 |
| 6,534,040 B2 | 3/2003 | Pandey et al. ........... 424/9.362 |
| 6,554,853 B2 | 4/2003 | Chen ......................... 607/88 |
| 6,580,228 B1 | 6/2003 | Chen et al. ............ 315/185 R |
| 6,602,274 B1 | 8/2003 | Chen ......................... 607/88 |
| 2001/0044623 A1 | 11/2001 | Chen ........................... 606/2 |
| 2001/0046983 A1 | 11/2001 | Pandey et al. ............. 514/185 |
| 2001/0049502 A1 | 12/2001 | Chen ..................... 604/167.06 |
| 2002/0010500 A1 | 1/2002 | Chen ......................... 607/89 |
| 2002/0049247 A1 | 4/2002 | Chen ......................... 514/410 |
| 2002/0087205 A1 | 7/2002 | Chen ......................... 607/88 |
| 2002/0127224 A1 | 9/2002 | Chen ....................... 424/130.1 |
| 2002/0127230 A1 | 9/2002 | Chen ....................... 424/178.1 |
| 2002/0198576 A1 | 12/2002 | Chen ......................... 607/88 |
| 2003/0018371 A1 | 1/2003 | Chen ......................... 607/88 |
| 2003/0109813 A1 | 6/2003 | Chen ............................. 60/2 |
| 2003/0114434 A1 | 6/2003 | Chen et al. ................ 514/185 |

FOREIGN PATENT DOCUMENTS

| | | |
|---|---|---|
| EP | 0175617 | 10/1991 |
| EP | 1334748 | 8/2003 |
| GB | 2323284 | 9/1998 |
| JP | 53084998 | 7/1978 |
| JP | 57185220 | 11/1992 |
| WO | 9200106 | 1/1992 |
| WO | 9300005 | 1/1993 |
| WO | 9311657 | 6/1993 |
| WO | 9313769 | 7/1993 |
| WO | 9324127 | 12/1993 |
| WO | 9532001 | 11/1995 |
| WO | 9606641 | 3/1996 |
| WO | 9731582 | 9/1997 |
| WO | 9732520 | 9/1997 |
| WO | 9732885 | 9/1997 |
| WO | 9740679 | 11/1997 |
| WO | 9746262 | 12/1997 |
| WO | 9806456 | 2/1998 |
| WO | 9808565 | 3/1998 |
| WO | 9814243 | 4/1998 |
| WO | 9820936 | 5/1998 |
| WO | 9824371 | 6/1998 |
| WO | 9824510 | 6/1998 |
| WO | 9832491 | 7/1998 |
| WO | 9832492 | 7/1998 |
| WO | 9832493 | 7/1998 |
| WO | 9833251 | 7/1998 |
| WO | 9846130 | 10/1998 |
| WO | 9847541 | 10/1998 |
| WO | 9850034 | 11/1998 |
| WO | 9850387 | 11/1998 |
| WO | 9852610 | 11/1998 |
| WO | 9856302 | 12/1998 |
| WO | 9903503 | 1/1999 |
| WO | 9406424 | 3/1999 |
| WO | 9918879 | 4/1999 |
| WO | 9920346 | 4/1999 |
| WO | 9939769 | 8/1999 |
| WO | 9952565 | 10/1999 |
| WO | 9958149 | 11/1999 |
| WO | 9966988 | 12/1999 |
| WO | 9967249 | 12/1999 |
| WO | 0015296 | 3/2000 |
| WO | 0027365 | 5/2000 |
| WO | 0029617 | 5/2000 |
| WO | 0036983 | 6/2000 |
| WO | 0041725 | 7/2000 |
| WO | 0041726 | 7/2000 |
| WO | 0041727 | 7/2000 |
| WO | 0041768 | 7/2000 |
| WO | 0052793 | 9/2000 |
| WO | 0103770 | 1/2001 |
| WO | 0105316 | 1/2001 |
| WO | 0115694 | 3/2001 |
| WO | 01015694 | 3/2001 |
| WO | 0143825 | 6/2001 |
| WO | 0151087 | 7/2001 |
| WO | 0178216 | 10/2001 |
| WO | 0178458 | 10/2001 |
| WO | 0198708 | 12/2001 |
| WO | 0217690 | 2/2002 |
| WO | 03052793 | 6/2003 |
| WO | 03061696 | 7/2003 |

OTHER PUBLICATIONS

Blaauwgeers et al., "Polarized Vascular Endothelial Growth Factor Secretion by Human Retinal Pigment Epithelium and Localization of Vascular Endothelial Growth Factor Receptors on the Inner Choriocapillaris", American Journal of Pathology, 155(2):421–428 (1999).

Boulton et al., "VEGF localization in diabetic retinopathy", Br J Ophthalmol, 82:561–568 (1998).

Certified English Translation of Japanese Patent Application No. Sho51–159879 (Japanese Kokai [Unexamined Patent] No. 53–84998), "Carcinostatic Method."

Certified English Translation of Japanese Kokai [Unexamined Patent] No. 57–185220, "Anti–Cancer Drug Having Chlorophyll Derivative Effective Component,".

Chen, J., "Next Generation Light Delivery System for Multi–Treatment Extended Duration Photodynamic Therapy (MED–PDT)", SPIE–Proceedings Series, 2972:161–167 (1997).

Chen et al., "New Technology for Deep Light Distribution in Tissue for Phototherapy", The Cancer J., 8(2):154–163 (2002).

De Jode et al., "A comparison of Novel Light Sources for Photodynamic Therapy", Lasers Med Sci, 12:260–268 (1997).

Dougherty, T.J., "A Brief History of Clinical Photodynamic Therapy Development at Roswell Park Cancer Institute", J. Clin. Laser Med. & Surg., 14(5):219–221 (1996).

Dougherty, T.J., "Photosensitization of malignant tumors", Sem. Sur. Oncol., 2:24–37 (1986).

Gagel, M. P., Photodynamic therapy with porphyrins (1997), available at http://www.dermatology.org/laser/pdt.html.

Henderson et al., "An in vivo quantitative structure–activity relationship for a congeneric series of pyropheophorbide derivatives as photosensitizers for photodynamic therapy", Cancer Res., 57:4000–4007 (1997).

Kessel et al., "Photosensitization with bacteriochlorins", Photochem. Photobiol., 58(2):200–203 (1993).

Kozyrev et al., "Effect of substituents in $OsO_4$ reactions of metallochlorins regioselective synthesis of isobacteriochlorins and bacteriochlorins", Tetrahedron Letters, 37(22):3781–3784 (1996).

Mizeret, et al., "Cylindrical Fiberoptic Light Diffuser for Medical Application", Lasers Surg. Med., 19:159–167 (1996).

Pandey et al., "Comparative in vivo sensitizing efficacy of porphyrin and chlorin dimers joined with ester, ether, carbon–carbon or amide bonds", *J. Molecular Recognition*, 9:118–122 (1996).

Prewett et al., "Antivascular Endothelial Growth Factor Receptor (Fetal Liver Kinase 1) Monoclonal Antibody Inhibits Tumor Angiogenesis and Growth of Several Mouse and Human Tumors", *Cancer Research*, 59:5209–5218 (1999).

Rimington et al., "Preparation and photosensitizing properties of hematoporphyrin ethers", *Free Rad. Res. Comms.*, 7(3–6):139–142 (1989).

Rungta et al., "Purpurinimides as photosensitizers: effect of the presence and position of the substituents in the in vivo photodynamic efficacy", *Bioorg. Medicinal Chem. Letters*, 10:1463–1466 (2000).

Schmidt–Erfurth et al., "Vascular targeting in photodynamic occlusion of subretinal vessels", *Ophthalmol.*, 101(12):1953–1961 (1994).

Spikes, J.D., "Porphyrins and related compounds as photodynamic sensitizers", Annals of the New York Academy of Sciences, 244:496–508 (1975).

Woodburn et al., "Evaluation of porphyrin characteristics required for photodynamic therapy", *Photochem. Photobiol.*, 55(5):697–704 (1992).

Adili et al., "Local delivery of photosensitizing drugs in arteries: a novel approach to photodynamic therapy for the prevention of intimal hyperplasia", *Proc. SPIE–INT. Soc. Opt. Eng.*, 2395:402–408 (1995) (Ger. Symp. Laser Angioplasty, 2nd, 1980).

Anonymous (1997) http://www.lumacare.com/, 2 pages.

Anonymous (May 1998) "The 1998 Photonics Circle of Excellence Award Winners", *Photonics Spectra*, pp. 95–96.

Article: "Photonics Application of High–Power Semiconductor Diode Laser Technology", *AFRL Technology Horizons*, 1(1), 35–36 (2000).

Barr et al., "Normal tissue Damage Following Photodynamic Therapy: Are There Biological Advantages?", Book: Photodynamic Therapy, Basic Principles and Clinical Applications, Barbara W. Henderson and Thomas J. Dougherty, (Eds.); Marcel Dekker, Inc. New York, pp. 201–216.

Bärwolff et al., "Semiconductor Diode Lasers: Research and Applications at the Max–Born–Institute", pp. 1–10 (1995).

Bayer et al., "Raw eggs and cancer therapy", *Science Spectra*, 12:34–41 (1998).

Beems et al., Photosensitizing properties of bacteriochlorophyllin a and bacteriochlorin a, two derivatives of bacteriochlorophyll a, Photochem. Photobiol. 46(5): 639–643 (1987).

Bellnier et al., Murine pharmacokinetics and antitumor efficacy of the photodynamic sensitizer 2-[1-hexyloxyethyl]-2-devinyl pyropheophorbide-a, J. Photochem. Photobiol. B: Biol. 20: 55–61 (1993).

Birchler et al., "Selective Targeting and Photocoagulation of Ocular Angiogenesis Mediated by a Phage–Derived Human Antibody Fragment", *Nature Biotechnol.*, 17:984–988 (1999).

Brower, V., "Tumor Angiogenesis—New Drugs on the Block", *Nature Biotechnology.*, 17:963–968 (1999).

Buda, Manuela, "Low–Confinement High–Power Semiconductor Lasers", Eindhoven University of Technology, The Netherlands (ed.), pp. 58–77 (1999).

Casalini et al., "Tumor Pretargeting: Role Of Avidin/Streptavidin On Monoclonal Antibody Internalization", *J.Nuclear Med.*, 38(9):1878–1381 (1997).

Cattel et al., "The Role of Conjugation Processes and Linking Agents in the Preparation of Molecular/Particulate Conjugates—a Review", *S.T.P. Pharma. Sci.*, 9(4):307–319 (1999).

Ciulla et al., "Changing therapeutic paradigms for exudative age–related macular degeneration: antiangiogenic agents and photodynamic therapy", *Exp. Opin. Invest. Drugs*, 8(12):2173–2182 (1999).

Dartsch et al., "Photodynamic therapy of vascular stenoses? Response of cultured human smooth muscle cells from non–atherosclerotic arteries and atheromatous plaques following treatment with photosensitizing porphyrins", *Proc. SPIE–INT. Soc. Opt. Eng.*, 1462:77–80 (1990).

Dictionary of Cell Biology, Second Edition (Lackie & Dow, eds., 1989), p. 17.

Dillon et al., "In Vitro and In Vivo Protection Against Phototoxic Side Effects of Photodynamic Therapy by Radioprotective Agents WR–2721 and WR–77913", *Photochemistry and Photobiology*, 48(2):235–238 (1988).

Dimitroff et al., "Anti–angiogenic activity of selected receptor tyrosine kinase inhibitors, PD166285 and PD173074: Implications for combination treatment with photodynamic therapy", *Investigational New Drugs*, 17:121–135 (1999).

Dougherty et al., Yearly Review "Photodynamic Therapy", *Photochem. Photobiol.*, 58(6):895–900 (1993).

Dougherty et al., Review "Photodynamic Therapy", *J. Nat. Cancer Inst.*, 90(12):889–905 (1998).

Dougherty, T.J., Photosensitization of malignant tumors, Seminars in Surgical Oncology 2:24–37 (1986).

Edamatsu et al., "One and Two–Photon Selective Excitation Spectroscopy of CuC1 Quantum Dots", *Review*, 17:15–16 (1998).

Fact Sheet: Laser Medical Pac, pp. 1–2 (1998).

Ferrario et al., "Antiangiogenic Treatment Enhances Photodynamic Therapy Responsiveness in a Mouse Mammary Carcinoma", *Cancer Research*, 60:4066–4069 (2000).

Fisher et al., "Simultaneous Two–Photon Activation of Type–1 Photodynamic Therapy Agents," *Photochemistry and Photobiology*, 66(2), 141–155 (1997).

Freiherr, G., "Advances in Photodynamic Therapy Lure Device Innovators", *Medical Device & Diagnostic Industry*, http://feedback@devicelink.com, 4 pages.

Fukuda, Mitsuo, *Reiability and Degradation of Semiconductor Lasers and LEDs*, Artech House, Inc., pp. 43–65, 115–118, and 134–136 (1991).

Gilson et al., "Therapeutic ratio of photodynamic therapy in the treatment of superficial tumours of skin and subcutaneous tissues in man", *J. Cancer*, 58:665–667 (1988).

Granville et al., "Photodynamic Treatment with Benzoporphyrin Derivative Monoacid Ring A Produces Protein Tyrosine Phosphorylation Events and DNA Fragmentation in Murine P815 Cells", *Photochem. Photobiol.*, 67(3):358–362 (1998).

Haas et al., "Phototherapy of Bladder Cancer: Dose/Effect Relationships," *Journal of Urology*, 136:525–528 (1986).

Henderson et al., An in vivo quantitative structure–activity relationship for a congeneric series of pyropheophorbide derivatives as photosensitizers for photodynamic therapy, Cancer Research 57: 4000–4007 (1997).

Jacka et al., "A Lamp for Cancer Phototherapy", *Aust. J. Phys.*, 36:221–226 (1983).

Jiang et al., "Selective Depletion of a Thymocyte Subset in Vitro with an Immunomodulatory Photosensitizer", *Clin. Immunol.*, 91(2):178–87 (1999).

Jiang et al., "Enhanced photodynamic killing of target cells by either monoclonal antibody or low density lipoprotein mediated delivery systems", *J. Controlled Release*, 19:41–58 (1992).

Kashtan et al., "Photodynamic Therapy of Colorectal Cancer Using a New Light Source from In Vitro Studies to a Patient Treatment", *Dis. Colon. Rectum.*, 39(4):379–383 (1996).

Kessel et al., Photosensitization with bacteriochlorins, Photochem. Photobiol. 58(2): 200–203 (1993).

Kozyrev et al., Effect of substituents in $OsO_4$ reactions of metallochlorins regioselective synthesis of isobacteriochlorins and bacteriochlorins, Tetrahedron Letters 37(22): 3781–3784 (1996).

Kreimer–Birnbaum, M., "Modified Porphyrins, Chlorins, Phthalocyanines, and Purpurins: Second–Generation Photosensitizers for Photodynamic Therapy", *Seminars in Hematology* 26(2):157–173 (1989).

Latham et al., "Biophotonics Applications of High–Power Semiconductor Diode Laser technology", pp. 1–3 (1998).

Lin et al., "Skin Necrosis due to Photodynamic Action of Benzoporphyrin Depends on Circulating Rather than Tissue Drug Levels: Implications for Control of Photodynamic Therapy", *Photochem. Photobiol.*, 68(4):575–583 (1998).

Marcus, S. L., Photodynamic therapy of human cancer, Proc. of the IEEE 80(6): 869–889 (1992).

Marcus, S.L., "Photodynamic Therapy of Human Cancer", *Proceedings of the IEEE*, 80(6):869–889 (1992).

Margaron et al., "Photodynamic therapy inhibits cell adhesion without altering integrin expression", *Biochimica et Biophysica Acta*, 1359:200–210 (1997).

McMillan et al., "Tumor growth inhibition and regression induced by photothermal vascular targeting and angiogenesis inhibitor retinoic acid", *Cancer Lett.*, 137:35–44 (1999).

Meerovich et al., "Photosensitizer for PDT based on phosphonate phthalocyanine derivative", *Proc. SPIE–INT. Scc. Opt. Engl.*, 2924:86–90 (1996).

Merck Manual of Diagnosis and Therapy, 17th edition (Beers & Berkow, eds., 1999), pp. 816–817 and 1654–1657.

Mew et al., "Ability of Specific Monoclonal Antibodies and Conventional Antisera Conjugated to Hematoporphyrin to Label and Kill Selected Cell Lines Subsequent to Light Activation", *Cancer Res.*, 45:4380–4386 (1985).

Mew et al., "Photoimmunotherapy: Treatment of Animal Tumors with Tumor–Specific Monoclonal Antibody–Hematoporphyrin Conjugates", *Journal of Immunology*, 130(3):1473–1477 (1983).

Middleton et al., "Synthetic Biodegradable Polymers as Medical Devices", *Medical Plastics & Biomaterials*, pp. 30–39 (1998).

Millson et al., "Ex–Vivo Treatment of Gastric Helicobacter Infection by Photodynamic Therapy", *J. of Photochemistry and Photobiology B: Biology*, 32:59–65 (1996).

Nakatani et al., "Chemistry and biochemistry of Chinese drugs. VII. Cytostatic pheophytins from silkworm excreta, and derived photocytotoxic pheophorbides", *Chem. Pharm. Bull.*, 29(8):2261–2269 (1981).

Nemoto et al., "Inhibition by a new bisphosphonate (YM175) of bone resorption induced by the MBT–2 tumour of mice", *Brit. J. Cancer*, 67(5):893–897 (1993).

North et al., "Viral Inactivation in Blood and Red Cell Concentrates with Benzoporphyrin Derivative", *Blood Cells* 18: 129–140 (1992).

Pandey et al., "Shedding some light on tumours", *Chem. Indust.*, 1998:739–743 (1998).

Pandey et al., Comparative in vivo sensitizing efficacy of porphyrin and chlorin dimers joined with ester, ether, carbon–carbon or amide bonds, J. Molecular Recognition 9: 118–122 (1996).

Parrish, J.A., "Photobiologic Consideration in Photoradiation Therapy", *Porphyrin Photosensitization*, Kessel, D. and T.M. Dougherty (Eds.) New York: Plenum Press, 1983 pp. 91–108.

Pittau et al., "An Inexpensive Light Source for Oncologic Photodynamic Therapy", *IEEE Eng. Med. Biol.*, pp. 105–106 (1998).

Renno et al., "Photodynamic Therapy Using Lu–Tex Induces Apoptosis In Vitro, and its Effect is Potentiated by Angiostatin in Retinal Capillary Endothelial Cells", *Investigative Opthalmol. & Visual Sci.*, 41(12):3963–3971 (2000).

Rimington et al., Preparation and photosensitizing properties by hematoporphyrin ethers, Free Rad. Res. Comms. 7(3–6): 139–142 (1989).

Ruebner et al., "Carrier Systems in PDT II: Accumulate Strategies of Biotin–Avidin Coupled Photosensitizers Developed On Cultured Tumor Cells", *SPIE*, 2625:328–32 (1996).

Rungta et al., Purpurinimides as photosensitizers: effect of the presence and position of the substituents in the in vivo photodynamic efficacy, Bioorg. Medicinal Chem. Letters 10: 1463–1466 (2000).

Savellano et al., "Pegylated BPD Verteporfin C225 Anti–EGF Receptor Direct Covalent Linkage Photosensitizer Immunoconjugates", *Photochem. Photobiol.*, 69:38S (1999).

Savitsky et al., "Avidin–Biotin System for Targeting Delivery of Photosensitizers and Other Cytotoxic Agents Into Malignant Tissues", *SPIE* 3191:243–53 (1997).

Schmidt et al., "Size–dependent Two–Photon Excitation pectroscopy of CdSe Nanocrystals", *Physical Review B*, 53(19):12629–12632 (1996).

Schmidt–Erfurth et al., "In Vivo Uptake of Liposomal Benzoporphyrin Derivative and Photothrombosis in Experimental Corneal Neovascularization", *Lasers in Surgery and Medicine*, 17:178–188 (1995).

Schmidt–Erfurth et al., In vivo uptake of liposomal benzoporphyrin derivative and photothrombosis in experimental corneal neovascularization, Lasers in Surgery and Med. 17: 178–188 (1995).

Schmidt–Erfurth et al., "Photodynamic therapy of subfoveal choroidal neovascularization: clinical and angiographic examples", *Graefe's Arch. Clin. Exp. Ophthamol.*, 236:365–74 (1998).

Schmidt–Erfurth et al., "Photodynamic Therapy of Experimental Choroidal Melanoma Using Lipoprotein–delivered Benzoporphyrin", *Opthalmol.*, 101:89–99 (1994).

Sharman et al., "Novel water–soluble phthalocyanines substituted with phosphonate moieties on the benzo rings", *Tetrahedron Lett.*, 37(33):5831–5834 (1996).

Sigsestad et al., "Chemical Modification of Normal Tissue Damage Induced by Photodynamic Therapy", *British Journal of Cancer*, 74(Suppl.37):S89–92 (1996).

Spikes, J.D., Porphyrins and related compounds as photodynamic sensitizers, Annals of the New York Academy of Sciences 244: 496–508 (1975).

Stedman's Medical Dictionary, 26th Edition, (Williams & Wilkens, 1995), pp. 268, 276–280, 726–727, 1165, 1182, and 1571–72.

Sternberg et al., "Porphyrin–based Photosensitizers for Use in Photodynamic Therapy", *Tetrahedron*, 54:4151–4202 (1998).

Su, F., Photodynamic Therapy: A Maturing Medical Technology, OE–Reports, SPIE, Feb. 2000, available at http://www.spie.org/web/oer/february/feb00/phototherapy.html.

Szeimies et al., "A New Light Source for PDT of Skin Lesions", http://www.lumacare.com/paper3.htm, 2 pages (after 1993).

Szeimies et al., "A Possible New Incoherent Lamp for Photodynamic Treatment of Superficial Skin Lesions", *Acta Derm Venereol*, 74:117–119 (1994).

Taber's Cyclopedic Medical Dictionary, 14th edition (C. L. Thomas, Ed.), Philadelphia: F.A. Davis Company, pp 63 (1983).

Tomio et al., "Effect of Hematoporphyrin and Red Light on AH–130 Solid Tumors in Rats", *ACTA Radiologica Oncol.*, 22:49–53 (1983).

Umemura et al., "Recent Advances in Sonodynamic Approach to Cancer Therapy," *Ultrasonics Sonochemistry*, 3:S187–S191 (1996).

Warwick, R.I., "Infinite Machines' Subsidiary Receives Positive Results in Photodynamic Therapy Tests", *BW Healthwire*, http://biz.yahoo.com/bw/97/06/18/imci_y000_1.html, 2 pages (1997).

Whitehurst et al., "Development of an Alternative Light Source to Lasers for Photodynamic Therapy: 1. Comparative In Vitro dose Response Characteristics", *Lasers in Med. Sci.*, 8:259–267 (1993).

Wieman et al., "(418) Photodynamic Therapy (PDT) of Locally Recurrent Breast Cancer (LRBC) with Lutetium Texaphyrin (Lutrin)", *American Society of Clinical Oncology*, 18:111A (1999).

Wilder–Smith et al., "(G1546) Photoeradication of *Helicobacter pylori* in Humans: Phase 1 Study", *AGA Abstracts Gastroenterology*, 116(4):A354 (1999).

Woodburn et al., Evaluation of porphyrin characteristics required for photodynamic therapy, Photochem. Photobiol. 55(5): 697–704 (1992).

Yamamoto, T., "Suppression of tumors by the photodynamic action of phytochlorin sodium", *Medicine and Biology*, 90(4):161–164, English translation and certificate of translation included, 4 pages (Apr. 10, 1975).

Yamamoto et al, "Photoradiation therapy, phytochlorin and visible light", *Prevention and Detection of Cancer, Part 1, Prevention. vol. 2, Etiology–Prevention Methods*, Proceedings of the Third International Symposium on Detection and Prevention of Cancer held Apr. 26, 1976 in New York, N.Y., 1(2):1789–1802 (1978).

Yamamoto et al., "Effect of phytochlorin on transplantable cancer cells", *Medicine and Biology*, 89(6):433–438, English translation and certificate of translation included, 7 pages (Dec. 10, 1974).

Yamamoto et al., "Photodynamic effects on the nucleic acids of cancer cells sensitized by sodium phytochlorin", *Medicine and Biology*, 90(6):397–400, English translation and certificate of translation included, 4 pages (Jun. 10, 1975).

Yumita et al., "The Combination Treatment of Ultrasound and Antitumor Drugs on Yoshida Sarcoma", *Japan J. Hyperthermic Oncology*, 3(2):175–182 (1987).

Yumita et al., "Sonodynamically Induced Antitumor Effect of Gallium–Porphyrin Complex by focused Ultrasound on Experimental Kidney Tumor", *Cancer Letters*, 112:79–86 (1997).

* cited by examiner

AMBULATORY PHOTODYNAMIC THERAPY

RELATED APPLICATIONS

This application is a divisional of allowed U.S. application Ser. No. 09/232,129, filed Jan. 15, 1999 now U.S. Pat. No. 6,454,789. The subject matter of this application is incorporated by reference in its entirety.

FIELD OF THE INVENTION

This invention relates generally to a light therapy device for activation of medicaments at one or more treatment sites within a living body, and more specifically, to photodynamic therapy devices adapted to reduce dislodgement risk over long treatment periods and enable a patient to be ambulatory without interruption of the therapy.

BACKGROUND

Photodynamic therapy (PDT) is a two-step treatment process that has been found to be effective in destroying a wide variety of cancers. PDT is performed by first systemically or topically administering a photosensitizer compound, and subsequently illuminating a treatment site with light in a waveband, which corresponds to an absorption waveband of the photosensitizer. The light energy activates the photosensitizer compound, causing it to destroy the diseased tissue.

Numerous systems have been proposed to effectively deliver the activating light to the treatment site. Examples of such systems can be found in U.S. Pat. Nos. 5,519,534 issued May 21, 1996 to Smith, et al., 5, 344,434 issued Sep. 6, 1994 to Talmore, and 4,693,556 issued Sep. 15, 1987 to McCaughen. The systems disclosed in these patents generally comprise a laser light source coupled to a proximal end of a flexible biocompatible optical fiber having a distal end adapted to be positioned within the body of a patient, either inside or adjacent to an internal treatment site. The optical fiber conducts and guides activating light from the laser light source to the treatment site at the distal end of the optical fiber. A diffuser enclosing the distal end of the optical fiber diffuses the light, and thus delivers the light to the treatment site at a uniform intensity to effect activation of the photosensitizer compound. In these systems, the diffuser may comprise a sphere positioned on the distal end of the fiber and having an inner partially reflective surface that aids in diffusing light transmitted through the sphere. Other light delivery devices can be found, for example, in U.S. Pat. Nos. 5,709,653 issued Jan. 20, 1998 to Leone, U.S. Pat. No. 5,700,243 issued Dec. 23, 1997 to Nariso, and U.S. Pat. No. 5,645,562 issued Jul. 8, 1997 to Hann, et al., and U.S. Pat. No. 4,998,930 issued Mar. 21, 1991 to Lundahl. While disclosing systems that are generally similar to the aforementioned systems, these references described diffusers that have an added component. The diffusers of these devices either alternatively or additionally incorporated transparent balloons mounted coaxially around the distal end of the optical fiber. Once the distal end is positioned at the treatment site, the balloon may be inflated in order to increase the area of the treatment site that will be exposed to the activating light, and in some cases, to effect or at least aid in the diffusion of the activating light. Once the light therapy provided by delivery of the light to the treatment site is completed, the balloon may be deflated, and the optical fiber removed from the body of the patient.

A conventional PDT treatment is of very short duration, on the order of minutes, and is typically used to treat superficial and small volume lesions. In order to apply PDT successfully against large lesions, which may be located subcutaneously, more extended treatment sessions must be undertaken. Extending the time of treatment overcomes tumor resistance and enables the extent of the treatment site to be greatly enlarged, thus allowing effective therapy of a much greater tumor volume. Indeed, destruction of a large tumor volume by extended duration PDT has been demonstrated in a clinical treatment. The treated patient suffered from a very large retroperitoneal tumor, which had eroded through the skin. The protruding tumor was treated by inserting multiple light emitting probes, such as is described in commonly assigned U.S. Pat. No. 5,445,608, into the substance of the tumor. The probes were energized for more than forty hours after orally administering a dose of a photosensitizer called aminolevulinic acid. This treatment resulted in destruction of just under one-half kilogram of tumor mass over the ensuing four weeks.

While adequate for some applications, the lasers, other high-powered light sources, and optical fibers in current use for administering PDT to a treatment site suffer from several drawbacks related to safety and their inability to accommodate the extended sessions necessary to effectively treat large tumors. First, high-powered sources such as dye lasers, laser diodes, large light emitting diode (LED) arrays, incandescent sources, and other electroluminescent devices are not efficient in converting electrical energy into light energy. They generate significant amounts of heat, and consume a substantial amount of electrical power. Prolonged use of high intensity light sources can lead to inadvertent tissue damage due to the effect of the high intensity light. Further, certain of these devices, e.g. laser light sources, generate sufficient heat that they must be cooled while activated. The need for cooling necessitates the incorporation of additional hardware such as fans or cooling units that draw additional power from the main power supply.

Second, the amount of power consumed by high intensity light sources requires that they be supplied with power from an alternating current (AC) line power source. Movement by the patient or attendance efforts by hospital personnel during the treatment period that cause the patient to move can inadvertently disconnect or damage the power cord, not only interrupting the treatment, but also creating a risk of electric shock. Further, being tethered to a substantially fixed power source limits the application of optical extended treatments, inasmuch as the patient will invariably need to move or be moved during the treatment period. Movement of the patient will likely cause the treatment to be interrupted and thus, render it less effective.

Third, none of the prior art techniques for rendering PDT to an internal treatment site through an optical fiber provides an anchoring mechanism to effectively secure the optical fiber and its distal end within the body of the patient at the treatment site. Any movements by the patient or attendance efforts by hospital personnel during the treatment period could inadvertently pull or dislodge the optical fiber unless it is secured in place. In many cases, while it is easy to disconnect a power cable from a light source to allow the patient to temporarily move about before resuming treatment, it is not practical to remove the optical fiber from the patient's body at that time, as well. Instead, the optical fiber must remain in place while the patient moves about. Without an effective mechanism for securing the optical fiber in the patient's body and at the treatment site while the patient moves, the risk of tissue damage is increased by such activity. Not only can the tissue be torn or severe bleeding occur when the patient moves, but if the dislodgement is not so severe, that it is noticed, the distal end of the optical fiber can be displaced away from the treatment site, so that light is delivered to the wrong area in the patient's body, resulting in possibly severe and unwanted destruction of normal tissue.

Fourth, the methodology of short duration high intensity illumination has drawbacks when applied to treat moderate to large size tumors. These drawbacks include depletion of oxygen necessary for the photodynamic destruction of the tissue that has absorbed the photosynthesizer, incomplete activation of the circulating photosensitizer, mis-timing of the illumination session so that the light therapy is not administered during the peak concentration of the photosensitizer drug in the tumor, and the possible recovery of sublethally injured tumor cells, which were not completely destroyed due to the short treatment time.

Currently, PDT procedures using laser light sources may be performed during an operation in which a treatment site is surgically exposed, and as such, the period available for administering light therapy is approximately one to two hours at most. The extent of tumor necrosis resulting from such an illumination period is on the order of 1 to 2 centimeters in a zone radially surrounding the optical fiber. Thus, several devices have been developed in an attempt to increase the duration of PDT treatments, to enable the light therapy to continue after an incision in a patient undergoing surgery has been closed. For example, a number of solid state laser devices have been developed for administering PDT that are semi-portable. These devices are large, heavy, and must be transported on wheeled carts or other movable furniture. Such "desktop" or semiportable devices suffer from the drawbacks enumerated above if employed for prolonged PDT treatment periods lasting hours. Furthermore, such light sources must remain connected to the wall power plug by power cables, and the optical fibers through which light produced by the laser is directed to an internal treatment site are prone to dislodgement.

Another light source device, disclosed in U.S. Pat. No. 5,616,140 issued Apr. 1, 1997 to Prescott, can be powered by rechargeable batteries and thus, can be worn by the patient. Because this device generates only low power laser light, and is not designed to be coupled to optical fibers for directing the light it produces to an internal treatment site, its use is limited to superficial light therapy, e.g., to treating skin lesions. High power lasers currently used for PDT require cooling hardware, and a corresponding power source. Due to weight and size considerations, it is clearly not practical for a patient to move about pushing a high power laser, a cooling unit, and battery power supplies for the equipment sufficient to provide for a prolonged treatment session.

Accordingly, there is a need for a PDT system to administer light therapy, which reduces the risk of optical fiber dislodgement and allows a patient to move about without interruption of the PDT therapy over treatment periods lasting hours.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

SUMMARY

Provided is a PDT device for efficacious treatment of relatively large tumors that are currently not treatable using conventional PDT delivery systems and methodologies and is specially adapted to reduce the risk of dislodging an optical fiber from a treatment site and when the patient moves about. The patient can thus be ambulatory without interruption of the light therapy over long treatment periods. In a preferred embodiment, the present invention comprises a belt or harness that supports and secures a lightweight rechargeable battery and a cold cathode fluorescent (CCF) tube powered thereby to a patient. The CCF tube is coupled to a proximal portion of the optical fiber. A distal portion of the optical fiber is provided with means for diffusing light as it exits the optical fiber. The distal portion of the fiber is adapted to be positioned at a treatment site within a patient's body by a medical practitioner. A balloon disposed at a distal end of the optical fiber can be inflated after the insertion of the optical fiber within the patient's body, to secure the distal portion of the fiber within the tissue at the treatment site; the balloon is deflated prior to the removal of the optical fiber, once administration of the light therapy is completed.

The present invention overcomes the limitations of the prior art PDT delivery devices in several respects. First, the use of a CCF tube provides increased effectiveness and efficiency compared to laser light sources. Light energy losses due to coupling of the light source to the optical fiber are minimized by employing a parabolic reflector and lens to focus the light into the proximal portion of the optical fiber. It is possible to obtain a greater zone of necrosis using non-laser light delivered to the tumor mass over a longer period of time, for example, 40 hours. Therefore, a CCF tube is preferred over other light sources, such as solid laser diodes, fiber lasers, LEDs, incandescent sources, halogen sources, polymeric luminescent devices or other electroluminescent devices, because CCF tube is generally more efficient in converting electrical power to light energy. As such, it not only generates a minimal amount of heat, but also consumes a minimal amount of power, thereby eliminating the need for cooling fans and large or substantially fixed power supplies. In contrast, the alternative light sources listed above suffer from lower conversion efficiencies, generate more heat, and require greater amounts of electrical power.

A second advantage is that the use of a CCF tube allows the present invention to be powered by a portable power supply that employs widely available and commonly used rechargeable batteries such as lithium ion, nickel metal hydride, and nickel cadmium rechargeable batteries, which are lightweight and inexpensive. In contrast, the need for at least some of the other types of light sources to be accompanied by cooling fans, and even cooling systems (with the need for an additional power supply to run the cooling system), makes it impractical for them to be adapted to a portable system, because they are too bulky, weigh too much, and are too expensive. It is not a trivial advantage for the present invention to be readily portable and free from being continuously linked to a stationary or permanent power source. As the present invention can be carried about by the patient on a belt or harness, there are no power cables, which can be severed or pulled from a fixed power source due to inadvertent movements by the patient. Thus, the risk of treatment interruption and electric shock is minimized. More importantly, the patient will be able to undergo optimal extended treatment sessions, as the patient will be able to move freely or be moved without interruption of the treatment. The ability of a CCF tube to be formed into various compact shapes, including "U"s, coils, spirals, and elongate forms, further facilitates the efficient administration of light to various correspondingly shaped treatment sites by the present invention and permits the system to be worn and transported by the patient easily and comfortably.

A third advantage provided by the present invention is that it enables a CCF tube to be easily coupled in light channeling relation to the proximal portion of at least one biocompatible optical fiber. The biocompatible optical fiber is flexible not only inasmuch as its distal portion can be easily positioned within the tissue of the patient at a treatment site, but also because it can accommodate movement of surrounding tissue associated with patient respiration and ambulation. A parabolic mirror positioned in partially surrounding relation to the CCF tube and a focusing lens positioned between the CCF tube and the proximal portion of the fiber cooperate to channel light into the proximal portion of the fiber. Specifically, the parabolic mirror reflects light from the CCF tube onto the focusing lens, which focuses the light into the proximal portion of the optical fiber. After the light travels through the optical fiber, it is diffused at the distal portion of the optical fiber by a diffuser of the types that are well known and documented in the art. The diffusion of the light emitted from the distal portion of the optical fiber enables the light to be administered more uniformly to the treatment site to activate the photosensitive compound previously administered. The length of the optical fiber is preferably limited to that necessary to reach the treatment site, in order to minimize light loss along the length of the optical fiber. The outer coating of the optical fiber is preferably opaque to light, in order to prevent light leaking from the optical fiber activating any photosensitizer absorbed by normal tissue along the length of the fiber. Additional biocompatible optical fibers may be connected to the parabolic mirror and focusing lens coupling the light into the proximal portions of the optical fibers or alternatively, may be spliced into the biocompatible optical fiber into which the light is focused.

A fourth advantage over the prior art devices is that it optionally includes anchoring means for securing the optical fiber and particularly, its distal portion within the body of the patient at the treatment site. The balloon mounted to the distal end of the optical fiber can be inflated with a pressurized fluid such as air that flows through a lumen that extends substantially parallel to and which is disposed within or adjacent to the optical fiber. This lumen is thus maneuverable with the optical fiber. The lumen runs substantially the length of the optical fiber, from the pressurized fluid source that is external to the patient's body to the balloon at the distal end of the optical fiber. After positioning the distal portion of the fiber within the tissue of the patient at the treatment site, the balloon is inflated to secure the distal end of the optical fiber in the tissue. The inflated balloon also tamponades any bleeding, which may occur at the distal end of the optical fiber during its insertion. Thus, any movement by the patient during the treatment will not dislodge the optical fiber or its distal portion because the balloon anchors the optical fiber in place. Similarly, movement of the distal portion of the optical fiber will thus be avoided, preventing light from being administered to healthy tissue that has absorbed the photosensitizer. Overall, the risk of damage to normal tissue is minimized, and the need for the patient to interrupt treatment before moving about is eliminated. Once treatment is complete, the balloon is deflated to facilitate removal of the optical fiber from the patient's body. It should be noted that for some applications, the distal portion of the optical fiber should preferably abut, rather than be embedded in the treatment site. This may be the case where, for example, it is undesirable or difficult to penetrate the tumor or diseased tissue. In such a situation, the balloon may be positioned at an intermediate point along the length of the optical fiber and/or in coaxially surrounding relation to the optical fiber, rather than at its distal end.

The above features and advantages of the present invention will be better understood upon a reading of the following detailed description with reference to the accompanying drawings.

BRIEF DESCRIPTION OF THE DRAWINGS

The foregoing aspects and many of the attendant advantages of this invention will become more readily appreciated as the same becomes better understood by reference to the following detailed description, when taken in con unction with the accompanying drawings, wherein.

DESCRIPTION OF AN EXEMPLARY EMBODIMENT

While the present invention will be described more fully hereinafter with reference to the accompanying drawings, it is to be understood that persons skilled in the art may modify the invention herein described while achieving the functions and results of the invention. Accordingly, the descriptions that follow are to be understood as illustrative and exemplary of specific structures, aspects and features within the broad scope of the present invention and not as limiting of such broad scope.

Figure 1:
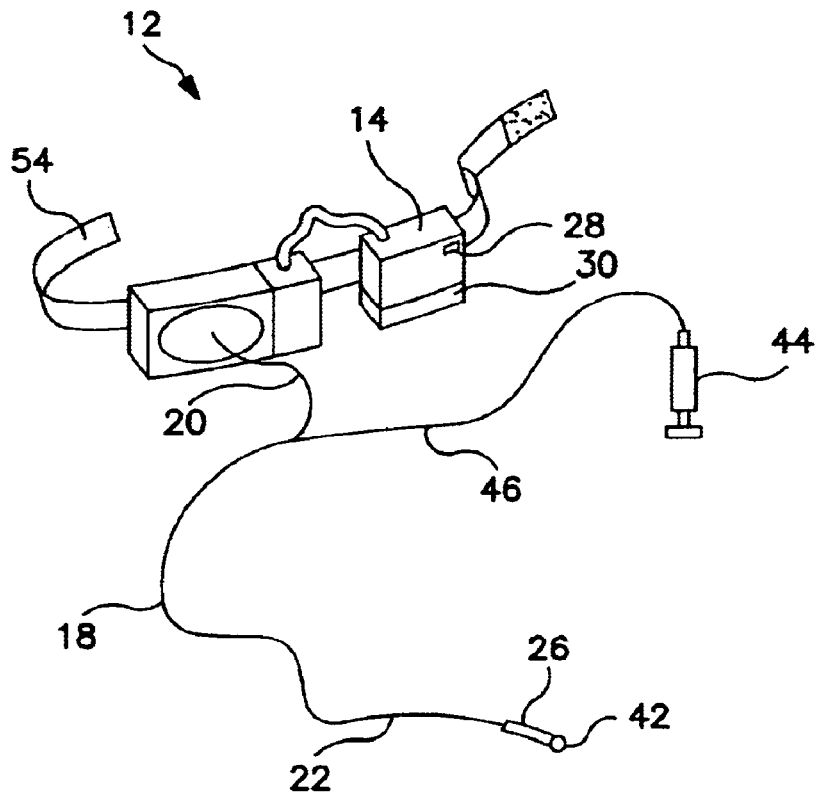
FIG. 1 is a perspective view of a patient portable PDT device according to a preferred embodiment of the present invention.
Figure 2:
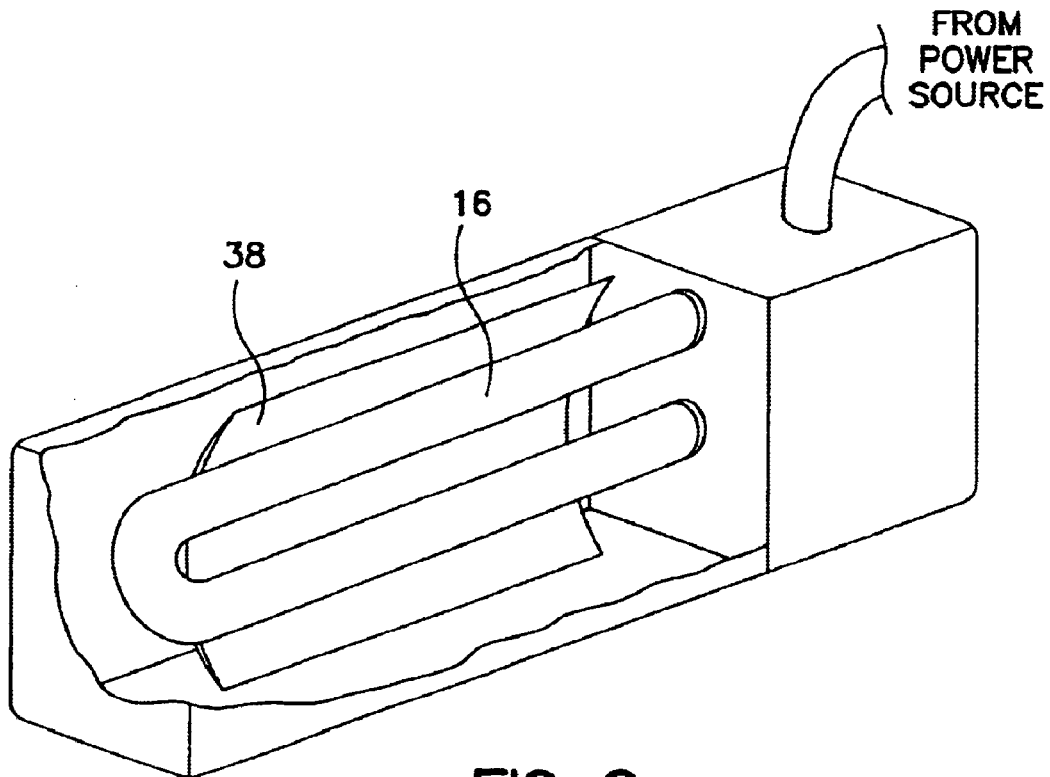
FIG. 2 is an expanded cut-away perspective view of a light source used in the patient portable PDT device, according to a preferred embodiment of the present invention.
Figure 3:
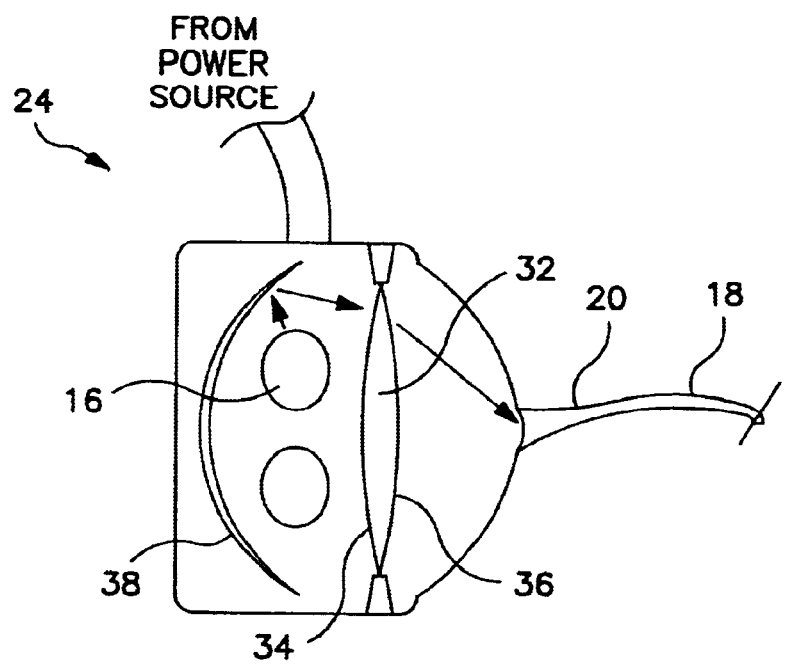
FIG. 3 is an expanded sectional view of light channeling coupling means of the patient portable PDT device, according to a preferred embodiment of the present invention.

Referring now to FIGS. 1, 2 and 3, a patient portable PDT device 12 according to the present invention comprises a power source, or lithium ion rechargeable battery pack 14; a light source, or CCF tube 16 formed into an elongated "U" shape (best shown in FIG. 2) and adapted to draw power from the battery pack 14; at least one biocompatible optical fiber 18 (only one is shown) having a proximal portion 20 and a distal portion 22, and adapted to channel light between the proximal portion 20 and the distal portion 22; and a coupling means 24 for coupling the CCF tube 16 in light channeling relation to the proximal portion 20 of the optical fiber 18 (best shown in FIG. 3). The optical fiber 18 is equipped with a diffusion means 26 (best shown in FIG. 1) for diffusing light as it exits the distal portion 22 of the optical fiber 18. The battery pack 14 includes a warning light 28 and backup power reserve 30.

It should be readily apparent to one skilled in the art, based on the instant disclosure, to alternatively use the following items in addition to or in place of their respective presently shown components, without departing from the broad scope of the present invention. For the lithium ion rechargeable battery pack 14, one may use one or more nickel cadmium rechargeable batteries, one or more nickel metal hydride rechargeable batteries, or fuel cells, any other type of electrical power source polymer batteries, one or more, other rechargeable batteries or non-chargeable batteries that are sufficiently compact and substantially lightweight to be readily portable, i.e., readily carried about by the patient. Such a power source should preferably operate at a relatively low or ambient temperature. In addition, instead of the CCF tube 16, one or more laser diodes, fiber lasers, LEDs, incandescent lights, halogen lights, polymeric luminescent devices, other types of fluorescent lights, discharge lamps, or other electroluminescent devices can be employed for the light source, including those having at least one of the characteristics of being substantially compact, substantially lightweight, operating at a substantially low temperature, or being self-contained so that the light source is suitable for a portable system that is readily carried about by the patient. For the diffusion means 26, any of the diffusers well known and documented in the prior art are suitable.

Referring now specifically to FIGS. 2 and 3, the preferred coupling means 24 employed to channel light emitted by the light source in the proximal end of the optical fiber comprises a focusing lens 32 having a convex receiver side 34 and a convex delivery side 36; and a parabolic mirror 38 positioned so that the CCF tube 16 is generally disposed at or adjacent to the focal point of the parabolic mirror. The focusing lens 32 is positioned between the CCF tube 16 and the proximal portion 20 of the optical fiber 18, so that the focusing lens receives the directly transmitted light from the CCF tube and the light reflected by the parabolic mirror 38 and focuses the light into the proximal end of the optical fiber 18. It should be readily apparent to one skilled in the art, based on the instant disclosure, to alternatively use in addition to or in place of the components disclosed for coupling means 24, one or more mirrors, concave lenses, or convex lenses, in appropriate configurations that channel light emitted by the light source into the proximal portion of the optical fiber, without departing from the broad scope of the present invention.

Figure 4:
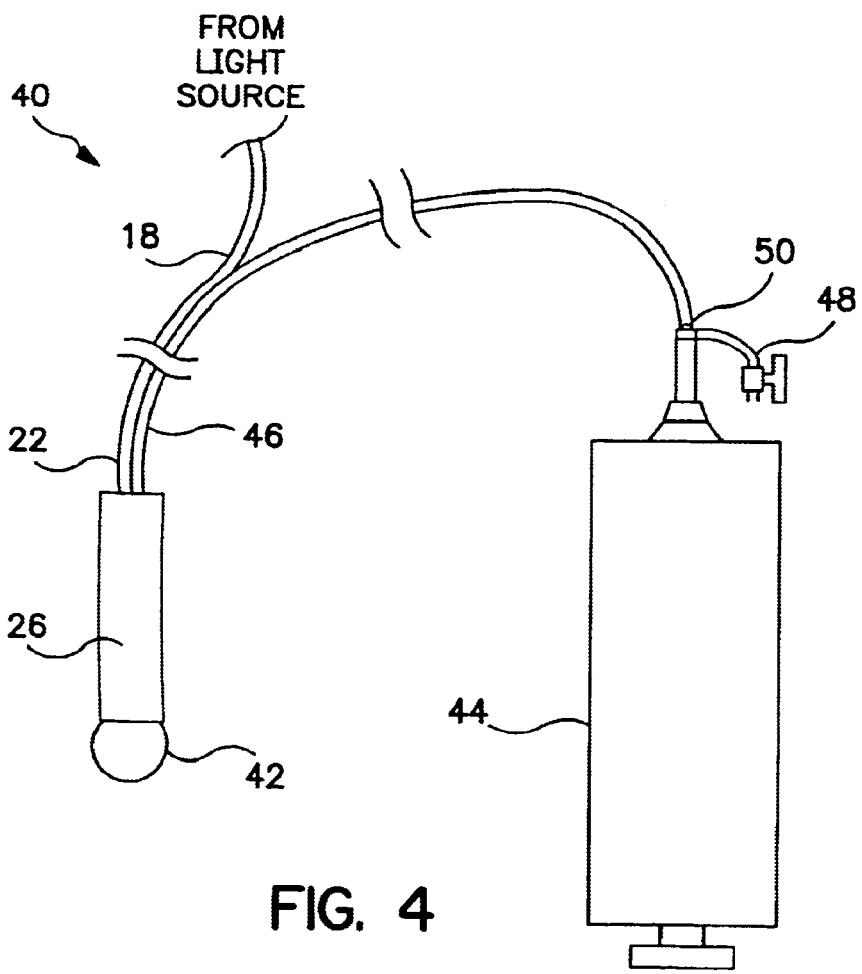
FIG. 4 is an expanded view of a distal portion anchoring means of the patient portable PDT device.

Referring now also to FIG. 4, the present invention further comprises an anchoring means 40 for anchoring the distal portion 22 of the optical fiber 18 within a patient's body. The anchoring means 40 preferably comprises a balloon 42 attached to the optical fiber 18, a pressurized air source 44 that may be a syringe that is configured to deliver pressurized air (or other pressurized fluid) to the balloon 42, a lumen 46 communicating between the air source 44 and the balloon 42, and a selection means, or control 48 and valve 50 for selectively delivering pressurized air from the pressurized air source 44 to the balloon 42 and exhausting the pressurized air from the balloon 42, so as to enable the selective inflation and deflation of the balloon. In this preferred embodiment, the optical fiber 18 has a distal end 52 on which the balloon 42 is mounted. The lumen 46 extends in substantially parallel relationship to the optical fiber 18 and runs substantially the length of the optical fiber 18, affixed to the side of the optical fiber over much of its length. Alternatively, the lumen is disposed within the optical fiber. Hollow optical fibers are well known in the optical fiber prior art.

It should be readily apparent to one skilled in the art, based on the instant disclosure, that one or more balloons (or other devices inflatable with pressurized fluids), lumens (or other channels capable of transporting gases or fluids), pressurized fluid sources, and/or other types of selection means (such as valves, switches, plugs or computer-, electrically- or mechanically-controlled components), can be employed in the present invention, in various configurations and combinations, without departing from the broad scope of the present invention. For example, a heat activated shape memory metal anchor, for example, one activated by heat developed by passing an electrical current therethrough, can be employed to hold the optical fiber in place.

Figure 5:
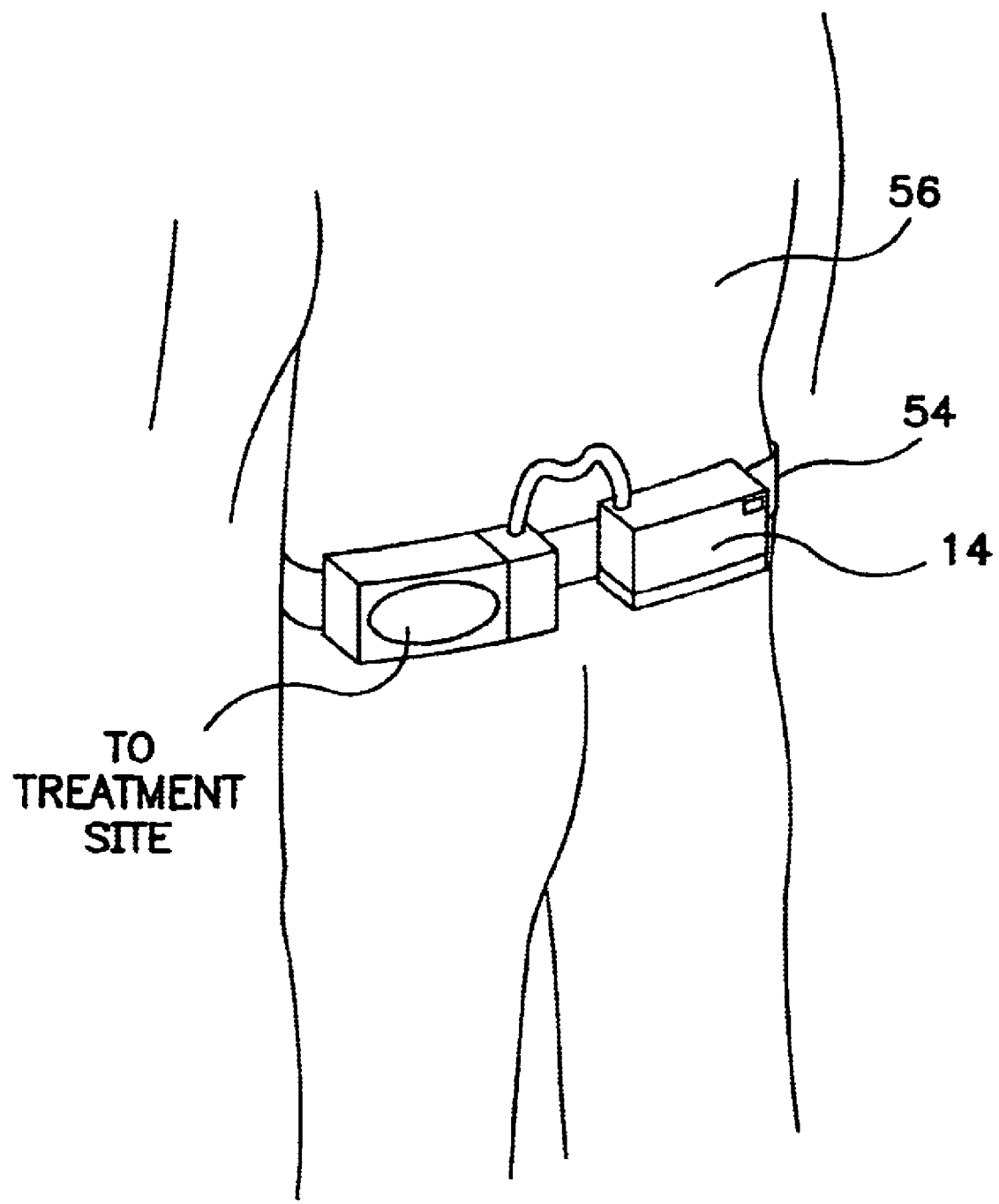
FIG. 5 is a perspective view of the patient portable PDT device being worn by a patient.

Referring now also to FIG. 5, the battery pack 14. COF tube 16 (best shown in FIG. 2) and coupling means 24 (best shown in FIG. 3) are mounted to means for enabling a patient to easily transport the battery pack 14, CCF tube 16, and coupling means 24, i.e., at least one belt 54 (only one is shown) and are thus supported and substantially secured to a patient's body 56 as shown. While the pressurized air source 44 (best shown in FIG. 4) can also be mounted to the belt 54 and thus supported and substantially secured to a patient's body 56, it is likely that the air source, preferably a syringe, will be used to initially inflate the balloon after the distal end of the optical fiber is properly positioned at the treatment site and thereafter be disconnected, provided that the pressurized fluid is retained within balloon until the optical fiber can be removed from the patient after the treatment is completed. It should be readily apparent to one skilled in the art, based on the instant disclosure, to alternatively use in addition to or in place of belt 54, one or more other belts, one or more harnesses, vests, straps, pockets, flaps, buckles, or hook-and-loop or other connection straps, in various combinations and configurations, to secure at least the light source and portable power supply to the patient's person, without departing from the broad scope of the present invention.

Figure 6:
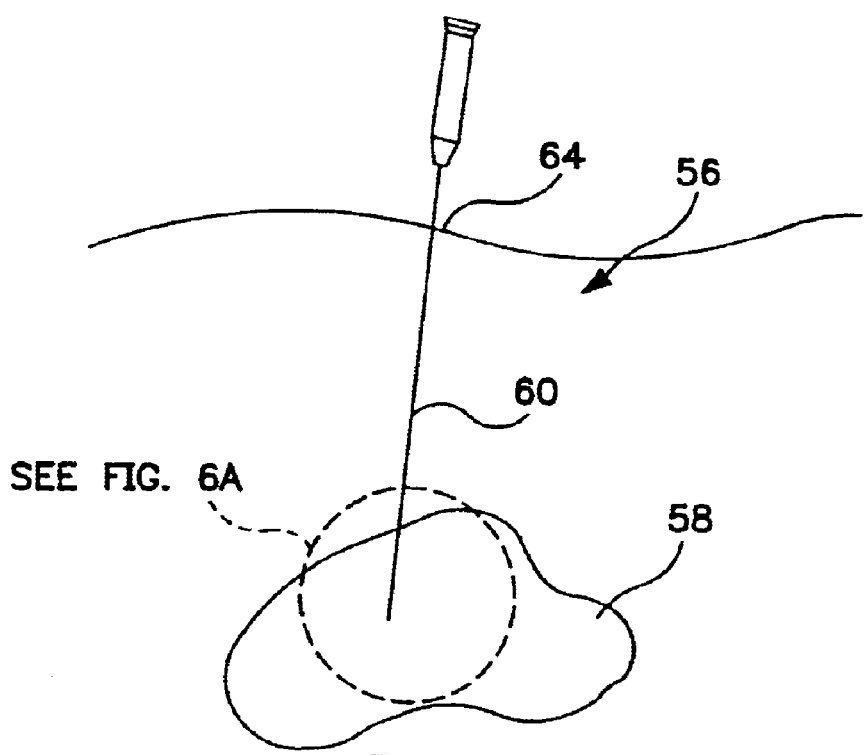
FIGS. 6 and 6A are cut away illustrations of the positioning of a needle having a peel away sheath that is employed for inserting an optical fiber used in the patient portable PDT device.
Figure 6A:
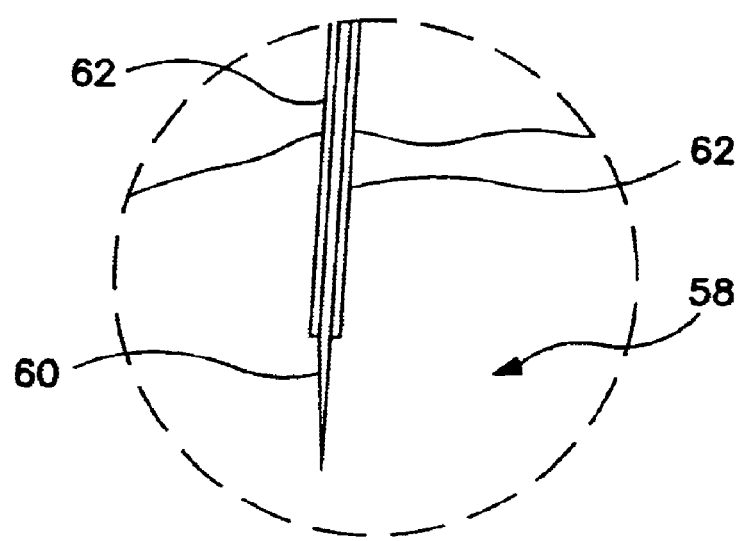
Figure 7:
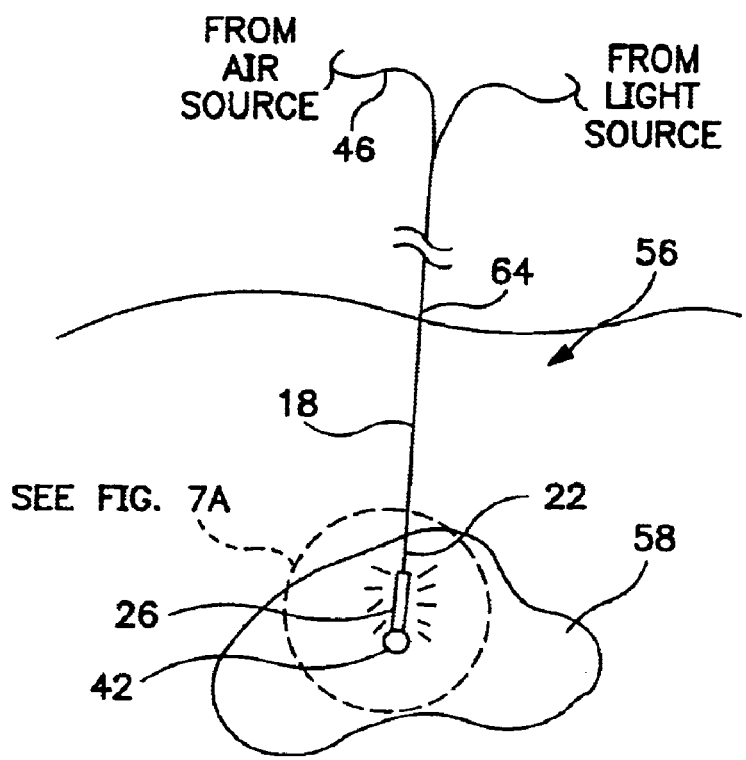
FIGS. 7 and 7A are cutaway illustrations of the positioning and anchoring of a distal portion of the optical fiber with balloon at the distal end of the optical fiber.

Referring now to FIGS. 6 and 6A, and 7, after the photosensitizer drug (not shown) is administered to the treatment site 58 within the patient's body 56 (not shown in full), a needle 60 having a peel away sheath 62 is inserted into the patient's body while observed using an appropriate imaging system (such as CT, Ultrasound, MRI, X-ray) to the treatment site 58 within the patient's body 56 (not shown in full). Though image guidance is preferred for achieving an accurate disposition of the optical fiber, it is optional and is not necessary, especially for disposition of the optical fiber to treat superficial lesions. The needle 60 is removed and the optical fiber 18 with the balloon 42 deflated is passed through the peel away sheath that was previously properly positioned at the treatment site. The position of the distal portion 22 is confirmed via the imaging modality used to pass the needle 60, and the peel away sheath 62 is pulled up and split apart. The position of the distal portion 22 is then reconfirmed. The proximal portion of the optical fiber 18 is secured to the skin of the patient at an exit point 64 by way of suture, adhesive tape, or other fixation means (not shown). The pressurized air source 44 (best shown in FIG. 4) is coupled to the lumen 46, and pressurized air from the pressurized air source 44 is delivered to the balloon 42 in volume sufficient to inflate the balloon 42 so as to anchor the distal portion 22 of the optical fiber 18 at the treatment site 58 and tamponade any bleeding, which may have occurred during the introduction of the optical fiber 18 into the patient's body. Once the balloon 42 is sufficiently inflated, the pressurized air source 44 is uncoupled from the lumen 46. The pressurized air is prevented from escaping from the lumen 46 by the valve 50 (best seen in FIG. 4). Any dislodgement or displacement of the optical fiber 18 or its distal portion 22 due to movement of the patient will be resisted by the inflated balloon 42.

Once the balloon 42 has been inflated, the patient fastens the belt 54 (best shown in FIG. 5), which supports and secures the battery pack 14, CCF tube 16 (best shown in FIG. 2), and coupling means 24 (best shown in FIG. 3) to the patient. The battery pack 14, CCF tube 16, and coupling means 24 collectively are sufficiently compact and lightweight to be easily transported by the patient, and movement about by the patient during extended treatments is thus greatly facilitated. The CCF tube 16 is coupled to the battery pack 14 so as to draw electrical power. The proximal portion 20 of the optical fiber 18 is coupled to the CCF tube 16 by the coupling means 24 (best shown in FIG. 3). Other coupling means are possible as well, such as those described in U.S. Pat. No. 5,769,844. Different lengths of optical fiber 18 are available so that the shortest length possible can be employed to minimize light loss. A slight amount of slack in the optical fiber is allowed so that bending, twisting, turning, and other movements by the patient are accommodated. To begin treatment, the CCF tube 16 is activated with electrical current from the battery pack. As best shown in FIG. 3, a quantity of light from the CCF tube 16 is reflected by the parabolic mirror 38 onto the receiver side 34 of the focusing lens 32. The focusing lens 32 focuses light from the parabolic reflector and from the CCF tube into the proximal portion 20 of the optical fiber 18. The light is channeled through the optical fiber 18 to the distal portion 22 of the optical fiber 18, where it exits the distal portion 22 and is diffused by the diffusion means 26. This diffused light is thus delivered to the treatment site 58 in a uniform manner.

The battery pack 14 preferably provides at least 2 to 3 hours of operating time, depending on the power consumption of the light source, before it must be recharged. Inasmuch as it is removable and modular, it can be immediately replaced with a fresh battery pack and later recharged without interruption of the therapy. Once the battery pack 14' begins to lose power, the warning light 28 on the battery pack 14 alerts the patient that the battery pack 14 must be replaced soon. The backup power reserve 30 provides the CCF tube 16 with power while the patient replaces the battery pack 14 with a fresh battery pack (not shown).

Once treatment is complete, or in the event that treatment must be halted prior the completion, the CCF tube 16 can be deactivated, the optical fiber 18 can be uncoupled from the coupling means 24, and the valve 50 can be opened to allow the pressurized air in the balloon 42 to escape, to deflate the balloon 42. Under the supervision of medically trained personnel, the suture or adhesive tape securing the proximal portion of the optical fiber 18, to the patient's body 56 at the exit point 64 can be removed, and the optical fiber 18 can be withdrawn from the patient's body.

Figure 8:
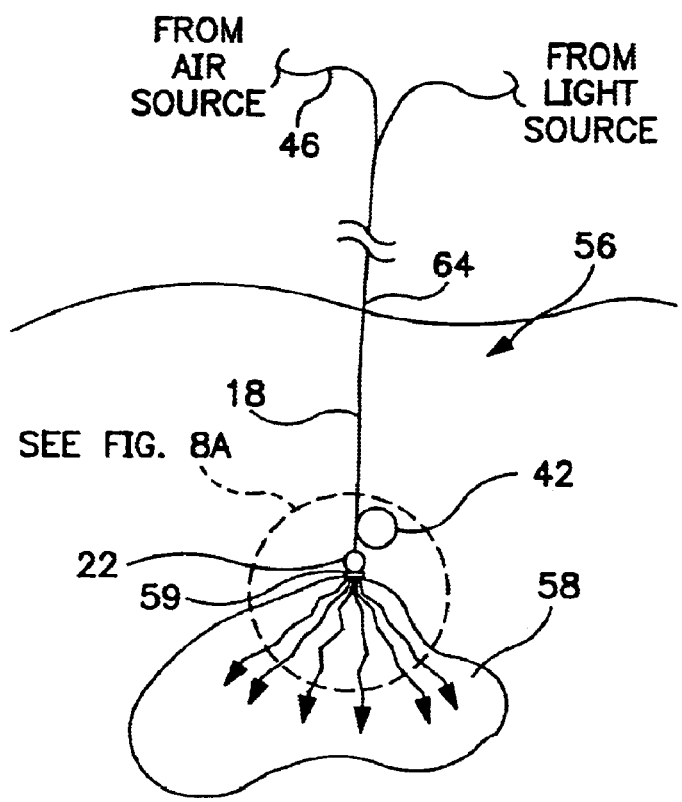
FIGS. 8 and 8A are cutaway illustrations of the positioning and anchoring of the distal portion of the optical fiber with balloon at any intermediate point along the optical fiber.
Figure 8A:
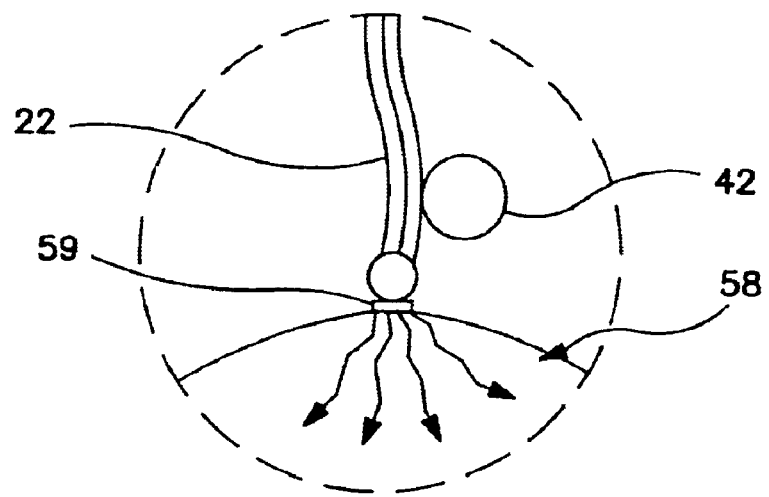

Referring now to FIGS. 8 and 8A, alternate preferred embodiments may incorporate a different positioning of the balloon 42, such as at an intermediate point along the length of the optical fiber 18 to enable the distal portion 22 of the optical fiber 18 to abut a treatment site 58 as shown, rather than to be inserted within the treatment site 58. In this embodiment, light is directed toward the treatment site by a microlens 59 attached to the distal end of the fiber optic. The lens 59 enables light to be focused onto the peripheral boundary of the treatment site and penetrate into its depths without actually having to insert the fiber optic into the treatment site. Administering light therapy to the surface of the treatment site is preferable when the site should not be punctured with a needle, such as in the care of a highly vascular lesion, which would bleed excessively if the needle passed through a blood vessel.

Referring again to FIGS. 1 and 7 and 7A, another aspect of the present invention is directed to a method for delivering light to a treatment site, comprising the steps of employing the power source, or battery pack 14 to energize the light source, or CCF tube 16; coupling the CCF tube 16 in light channeling relation to the proximal portion 20 of the biocompatible optical fiber 18; positioning the distal portion 22 of the optical fiber at the treatment site 58 within a patient's body; and administering the light through the optical fiber 18 to the treatment site 58. More specifically, the CCF tube 16 can be coupled in light channeling relation to the proximal portion by the coupling means 24 described in detail above and shown in FIG. 3. As noted above, it should be readily apparent to one skilled in the art, based on the instant disclosure that in addition to or in place of the presently shown coupling means 24, one or more mirrors, concave lenses, or convex lenses, in varying configurations can be used to channel the light into the optical fiber, without departing from the broad scope of the present invention. The distal portion 22 can be positioned at the treatment site 58 in the manner outlined in detail above and shown in FIGS. 6 and 6A, where a needle 60 having a peel away sheath 62 is passed under image guidance (such as CT, Ultrasound, X-ray) to the treatment site 58. After the needle 60 is withdrawn, the optical fiber 18 with the balloon 42 deflated is inserted through the peel away sheath. The position of the distal portion 22 is confirmed via the imaging modality used to position the needle 60, and the peel away sheath 62 is pulled up and split apart. The position of the distal portion 22 is then reconfirmed. It should be readily apparent to one skilled in the art, based on the instant disclosure, that alternative steps maybe used in addition to or in place of those described above, without departing from the broad scope of the present invention.

Figure 9:
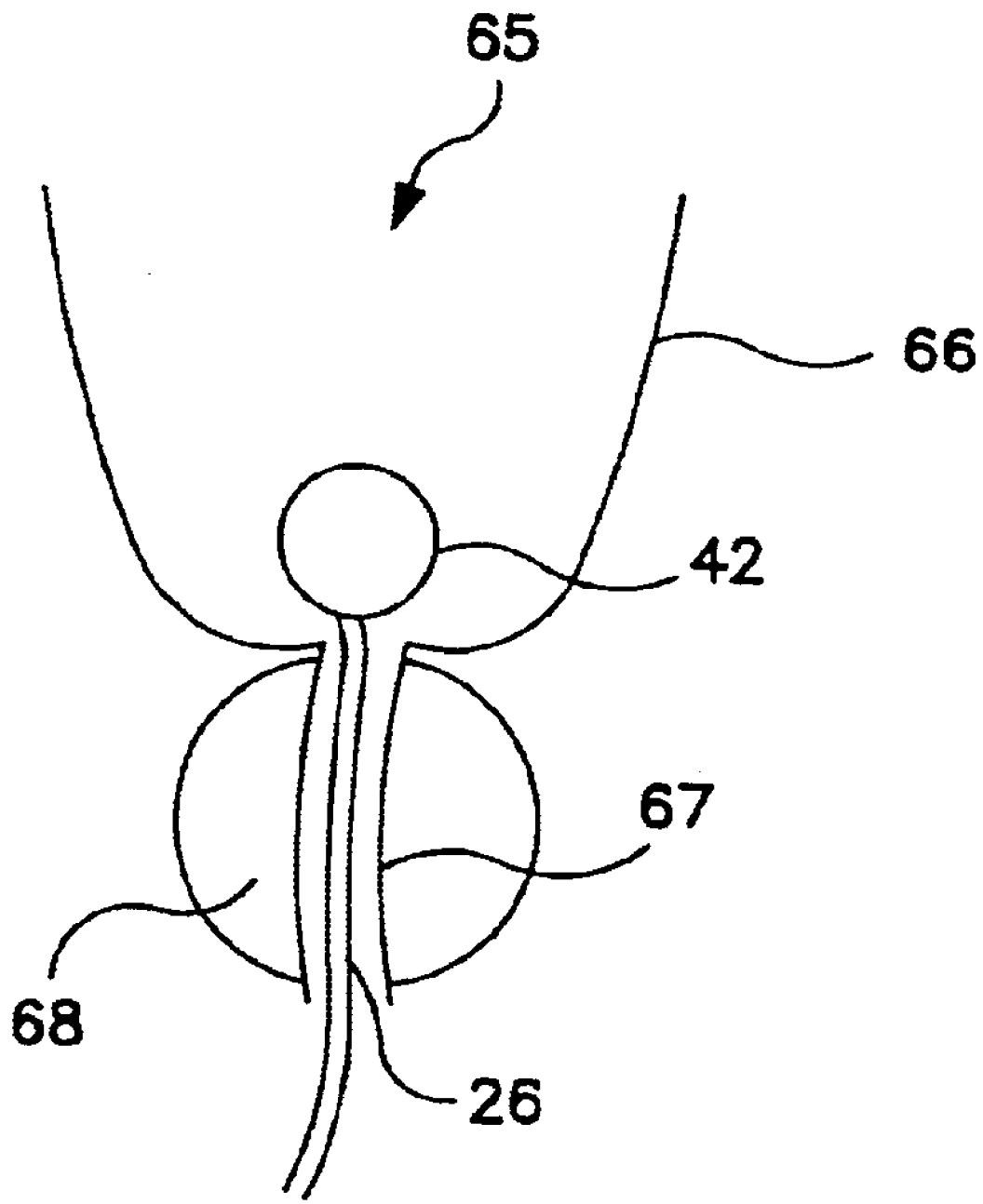
FIG. 9 is a cutaway illustration of the positioning and anchoring of the distal portion of the optical fiber in the bladder, with the light diffuser portion of the optical fiber disposed in the prostatic portion of a patient's urethra.

FIG. 9 illustrates treatment of bladder wherein the balloon 42 is inflated on the inside of the bladder wall 66 to keep the diffusion means 26 properly inserted in the urethra 67. The prostate gland 68 is also schematically represented.

Referring now again also to FIG. 4, another aspect of the present invention is directed to a method for anchoring the distal portion 22 of the optical fiber 18 at the treatment site 58. This method includes the steps of mounting the balloon 42 to the optical fiber 18; coupling the pressurized air source 44, configured to deliver pressurized air, in selective fluid communication with the balloon 42; positioning the balloon 42 (deflated) with the distal portion 22 into the treatment site 58; and activating the pressurized air source 44 to inflate the balloon 42 after positioning of the distal portion 22 of the optical fiber at the treatment site 58. More specifically, the pressurized air source 44 can be selectively coupled in fluid communication to the balloon 42 by the lumen 46 described in detail above, and employing the control 48 and valve 50 to control the inflation and deflation of the balloon, as described.

Figure 7A:
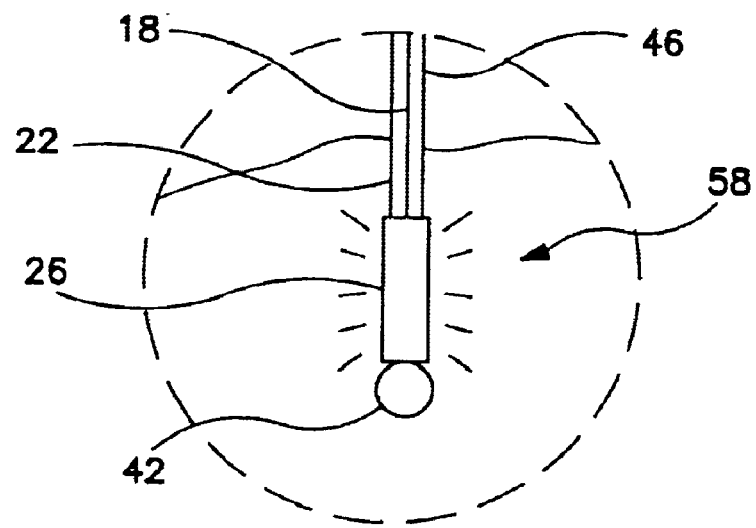

As further explained above, the balloon 42 may be positioned at the distal end 52 of the optical fiber 18 as shown in FIGS. 7 and 7A, or at any intermediate point along the length of the optical fiber 18 as shown in FIGS. 8 and 8A.

As noted above, it should be readily apparent to one skilled in the art, based on the instant disclosure, to alternatively use in addition to or in place of the components described for anchoring means 40, one or more balloons (or other devices inflatable by gases or fluids), lumens (or other channels capable of transporting gases or fluids), pressurized fluid sources (or other gas or fluid sources), and selection means (such as valves, switches, plugs, or computer-, mechanically- or electrically-controlled components, such as shape memory metal anchoring devices), in various configurations and combinations, without departing from the broad scope of the present invention.

Referring now again also to FIG. 5, yet another aspect of the present invention pertains to a method for securing the battery pack 14 and the CCF tube 16 to a patient. This method comprises the steps of securing the battery pack 14 and the CCF tube 16 to the belt 56 and attaching the belt 56 to a patient, as shown in FIG. 5. As noted above, it should be readily apparent to one skilled in the art, based on the instant disclosure, to alternatively use in addition to or in place of the belt 54, one or more other belts, harnesses, vests, straps, pockets, flaps, buckles, or hook-and-loop straps, or other connectors, in various combinations and configurations, without departing from the broad scope of the present invention.

Although the present invention has been described in connection with the preferred form of practicing it and in regard to alternative embodiments, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

What is claimed is:

1. A method for delivering light to a treatment site of a patient to administer a light therapy thereto, comprising the steps of:

providing a patient portable light therapy device, the patient portable light therapy device including:
   a portable power source that stores electrical energy;
   a light source coupled to said portable power source and adapted to be energized thereby, wherein said light source is adapted for use in a light therapy occurring over a period of time of at least two hours, and
   at least one optical fiber having a proximal portion coupled to the light source and a distal portion adapted to be disposed at a treatment site within a patient's body, said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body;
   positioning the distal portion of the at least one optical fiber at the treatment site;
   securing the patient portable light therapy device to the patient, thereby enabling the patient to be ambulatory, the patient portable light therapy device moving about with the patient;
   energizing the light source with the portable power source; and
   administering the light therapy to the treatment site with the patient portable light therapy device, such that ambulatory motion of the patient does not interrupt the administration of the light therapy to the treatment site.

2. The method of claim 1, further comprising the step of securing the distal portion of the at least one optical fiber at the treatment site.

3. The method of claim 2, wherein the step of securing of the distal portion of the at least one optical fiber comprises the step of: inflating a balloon attached to the optical fiber and implanted within the patient's body with a pressurized fluid after positioning the distal portion of the at least one optical fiber at the treatment site.

4. The method of claim 1, wherein the step of energizing comprises the step of energizing the light source without providing cooling.

5. The method of claim 1, wherein the step of securing comprises the steps of:
   securing the patient portable light therapy device to one of a belt and a harness; and
   attaching the one of the belt and the harness to the patient.

6. The method of claim 1, wherein the light source is a non-laser light source.

7. The method of claim 6, wherein the light source comprises a cold cathode fluorescent tube.

8. The method of claim 6, wherein the step of administering the light therapy to the treatment site comprises diffusing light to the treatment site through a diffuser.

9. The method of claim 8, further comprising the step of anchoring the distal portion of the at least one optical fiber within the patient's body.

10. The method of claim 1, wherein the step of administering the light therapy comprises the step of administering the light therapy continuously for at least two hours.

11. The method of claim 1, wherein the step of providing further comprises the step of providing a patient portable light therapy device wherein the light source comprises:
    a light emitting element operating without a cooling system;
    a focusing lens; and
    a parabolic mirror positioned adjacent to said light emitting element so as to reflect a quantity of light from said light emitting element onto the focusing lens, wherein the focusing lens is disposed between said light emitting element and a proximal portion of die optical fiber and is adapted to receive the quantity of light, transmit a portion of the quantity of light, and focus at least part of the portion of the quantity of light into the proximal portion of the at least one optical fiber.

12. The method of claim 1, wherein the portable light source includes a light emitting element, a focusing lens, and a parabolic mirror positioned adjacent to the light emitting element so as to reflect a quantity of light from the light emitting element onto the focusing lens; and wherein the focusing lens is disposed between the light emitting element and a proximal portion of the at least one optical fiber and is adapted to receive the quantity of light, transmit a portion of the quantity of light, and focus at least a part of the portion of the quantity of light into the proximal portion of the at least one optical fiber, without requiring cooling of the light emitting element with a cooling system.

13. A method for administering a photodynamic therapy, the method comprising the steps of:
    providing a patient portable light therapy device, the patient portable light therapy device including:
    a portable power source that stores electrical energy;

a portable light source coupled to said portable power source and adapted to be energized thereby, wherein said light source is adapted for use in a light therapy occurring over a period of time of at least two hours;

at least one optical fiber having a proximal portion coupled to the light source and a distal portion adapted to be disposed at a treatment site within a patient's body, said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body;

positioning the distal portion of the at least one optical fiber at the treatment site, wherein the treatment site is within a patient's body external to a vascular lumen of the patient's body;

securing the patient portable light therapy device to the patient, thereby enabling the patient to be ambulatory, the patient portable light therapy device moving with the patient substantially without hindering ambulatory movement of the patient;

energizing the light source with the portable power source for a period of time required to effect the photodynamic therapy; and enabling the patient to be ambulatory while the light source is energized, so that the ambulatory movement of the patient does not interrupt the photodynamic therapy.

14. The method of claim 13, wherein the method further comprises the step of anchoring the at least one optical fiber within the patient's body.

15. The method of claim 13, further comprising the step of diffusing light exiting from the distal portion of the at least one optical fiber.

16. The method of claim 13, wherein the light source includes a light emitting element, a focusing lens, and a parabolic mirror positioned adjacent to the light emitting element so as to reflect a quantity of light from the light emitting element onto the focusing lens; and wherein the focusing lens is disposed between the light emitting element and a proximal portion of the at least one optical fiber and is adapted to receive the quantity of light, transmit a portion of the quantity of light, and focus at least a part of the portion of the quantity of light into the proximal portion of the at least one optical fiber, without requiring cooling of the light emitting element with a cooling system.

* * * * *

UNITED STATES PATENT AND TRADEMARK OFFICE
CERTIFICATE OF CORRECTION

PATENT NO. : 6,986,782 B2
APPLICATION NO. : 10/211784
DATED : January 17, 2006
INVENTOR(S) : Chen et al.

Page 1 of 1

It is certified that error appears in the above-identified patent and that said Letters Patent is hereby corrected as shown below:

| | |
|---|---|
| On Title Page Item (75) "Inventors", Fifth Reference | "Issaquam" should read --Issaquah-- |
| Title Page, Page 4, (56) "Other Publications", Column 2, line 3 | "1878" should read --1378-- |
| Column 1, line 33 | "McCaughen" should read --McCaughan-- |
| Column 8, line 20 | "COF" should read --CCF-- |
| Column 8, line 44 | after "7" insert --and 7A-- |
| Column 9, line 44 | " pack 14'" should read --pack 14-- |
| Column 10, line 44 | "bladder" should read --bladder 65-- |
| Column 12, line 8 (Claim 3, line 1) | after "securing" delete "of" |

Signed and Sealed this

Nineteenth Day of September, 2006

JON W. DUDAS
*Director of the United States Patent and Trademark Office*